(12) United States Patent
Loveridge (10) Patent No.: US 7,314,610 B2
(45) Date of Patent: Jan. 1, 2008

(54) DENTAL COMPOSITIONS HAVING ANTI-STOKES UP CONVERTERS AND METHODS OF USE

(75) Inventor: Dan Loveridge, Sandy, UT (US)

(73) Assignee: Ultradent Products, Inc., South Jordan, UT (US)

( * ) Notice: Subject to any disclaimer, the term of this patent is extended or adjusted under 35 U.S.C. 154(b) by 303 days.

(21) Appl. No.: 11/066,013

(22) Filed: Feb. 25, 2005

(65) Prior Publication Data

US 2006/0193779 A1     Aug. 31, 2006

(51) Int. Cl.
*A61B 5/00* (2006.01)
*A61C 5/08* (2006.01)
(52) U.S. Cl. ................... 424/9.7; 433/222.1
(58) Field of Classification Search ............. 424/9.6
See application file for complete search history.

(56) References Cited

U.S. PATENT DOCUMENTS

| | | | | |
|---|---|---|---|---|
| 3,992,515 A | | 11/1976 | Johnson | 424/7 |
| 4,600,389 A | * | 7/1986 | Schwartz | 433/217.1 |
| 4,875,858 A | | 10/1989 | Jefferies | 433/226 |
| 4,954,414 A | | 9/1990 | Adair | 430/138 |
| 5,102,461 A | | 4/1992 | Rheinberger | 106/35 |
| 5,541,012 A | | 7/1996 | Ohwaki | 428/690 |
| 5,581,090 A | | 12/1996 | Goudjil | 250/474.1 |
| 5,607,621 A | | 3/1997 | Ishihara | 252/301.36 |
| 5,698,020 A | * | 12/1997 | Salz et al. | 106/35 |
| 5,754,570 A | | 5/1998 | Goh | 372/6 |
| 5,782,638 A | | 7/1998 | Warren | 433/206 |
| 5,891,361 A | | 4/1999 | Kane | 252/301.4 H |
| 6,117,362 A | | 9/2000 | Yen | 252/301.4 R |
| 6,159,686 A | | 12/2000 | Kardos | 435/6 |
| 6,287,993 B1 | * | 9/2001 | Fu et al. | 501/5 |
| 6,384,099 B1 | | 5/2002 | Ostler et al. | |
| 6,444,725 B1 | | 9/2002 | Trom | 523/118 |
| 6,499,995 B1 | | 12/2002 | Schwartz | 433/6 |
| 6,528,555 B1 | | 3/2003 | Nikutowski | 523/116 |
| 6,599,444 B2 | | 7/2003 | Burnell-Jones | 252/301.36 |
| 6,613,137 B2 | * | 9/2003 | Egger et al. | 106/31.65 |
| 6,670,436 B2 | | 12/2003 | Burgath | 526/213 |
| 6,749,773 B2 | | 6/2004 | Emanuel | 252/301.36 |
| 2002/0185634 A1 | | 12/2002 | Marder | 252/582 |
| 2004/0196538 A1 | * | 10/2004 | Burgener et al. | 359/341.5 |

FOREIGN PATENT DOCUMENTS

DE     19646037 A1     5/1998

OTHER PUBLICATIONS www.henryschein.com, dental supply catalog cover 2006, p. 1, Apr. 18, 2007.*
www.henryschein.com, dental supply catalog 2006, p. 184-185 (2 sheets), Apr. 18, 2007.*
J. Esthet. Dent. 2000;12(1):38-45 PMID: 11323832, abstract only.
J. Dent. Res. Apr. 2003;82(4):312-7 PMID: 12651938, abstract only.

* cited by examiner

*Primary Examiner*—Michael G. Hartley
*Assistant Examiner*—GiGi Huang
(74) *Attorney, Agent, or Firm*—Workman Nydegger

(57) ABSTRACT

A dental composition can include at least one polymerizable resin and at least one anti-stokes up converter. Alternatively, a two-part composition can include at least one dental composition configured for placement onto a person's tooth, and at least one anti-stokes up converter to be combined with the at least one dental composition. The dental composition can be formulated to blend with a person's tooth, and also be capable of changing color to be distinguishable from the tooth when exposed to long wavelength light. The dental composition can be used in a method for performing a dental procedure by applying the dental composition to a tooth, and exposing the dental composition to long wavelength light. Accordingly, the dental composition can aid a dental professional in distinguishing between the location of the dental composition and the tooth.

7 Claims, 6 Drawing Sheets

DENTAL COMPOSITIONS HAVING ANTI-STOKES UP CONVERTERS AND METHODS OF USE

CROSS-REFERENCE TO RELATED APPLICATIONS

This United States Patent Application cross-references two other United States Patent Applications filed simultaneously herewith on Feb. 25, 2005, entitled, respectively, DENTAL COMPOSITIONS HAVING DUAL DENTAL DIAGNOSTIC CAPABILITIES AND METHODS OF USE with Dan Loveridge, Peter M. Allred and Neil T. Jessop as inventors, Ser. No. 11/065,747, Express Mail Label No. EV462385885US; and DENTAL COMPOSITIONS HAVING A PHOSPHORESCENT MATERIAL AND METHODS OF USE with Dan Loveridge as inventor, Ser. No. 11/065,744, Express Mail Label No. EV462385942US; which applications are incorporated herein in their entirety.

BACKGROUND OF THE INVENTION

1. The Field of the Invention

The present invention relates to dental compositions that include anti-stokes up converters. More particularly, the present invention relates to combining anti-stokes up converters with sealants, varnishes, restoratives, adhesives, bonding agents, cements, composites, veneers, and crowns for use in dental diagnostic applications.

2. The Relevant Technology

Teeth are important anatomical features that can be seen during normal daily activities. When people smile or converse with each other, their teeth are usually exposed and observable. While the colors, shapes, and arrangement of a person's teeth may not have been important in the past, aesthetically pleasing teeth are becoming more desirable and almost mandatory in developed societies. In part, advances in dentistry and the availability of dental cosmetics has provided people with the ability to have their imperfect teeth reshaped, colored, and/or restored to near perfection.

Dental professionals have used a variety of dental compositions to fix teeth defects such as cavities or broken teeth. Originally, fillings, crowns, and other dental restorative compositions had colors that contrasted or did not blend with a patient's tooth or surrounding teeth. Recently, patients have begun to demand dental compositions that blend with the color of their teeth to produce a more natural visual effect. This demand may have partially been a result of the stigmatism associated with discolored teeth, and the social benefits of having an aesthetically pleasing smile.

In response, various dental compositions have been produced that blend with the color of a patient's teeth. These dental compositions can vary in color so that they can be matched to different colors and shades of teeth. Also, some compositions have been designed to be applied to the teeth in order to provide or enhance a natural white smile. These teeth-blending compositions are aesthetically pleasing because they can blend with existing teeth or make the teeth appear more perfect.

While patients have had favorable responses to teeth-blending dental compositions, it has been difficult for some dental professionals to work with these compositions. A negative consequence arising from the teeth-blending compositions has resulted in dental professionals not being able to adequately distinguish the dental composition from the underlying tooth. As such, an attempt to remove or modify the dental composition may result in damaging the tooth because portions of the tooth may accidentally be removed. While dental compositions that blend with teeth can provide short-term aesthetic benefits, the long-term consequences can include damaging the teeth when the composition has to be removed, repaired, or replaced.

Therefore, what is needed is an improved dental composition that can be formulated to visually blend with the tooth and surrounding teeth, and which can temporarily change colors in response to a specific stimulus.

BRIEF SUMMARY OF EMBODIMENTS OF THE INVENTION

Generally, an embodiment of a color changing dental composition in accordance with the present invention is capable of visually blending with a color of a person's tooth. Accordingly, the dental composition can include at least one polymerizable resin and be configured for placement on a person's tooth. Additionally, at least one anti-stokes up converter is admixed into the dental composition. As such, the dental composition is capable of converting absorbed IR-light into emitted visible light (e.g., colored light) so that the dental composition temporarily changes color and is distinguishable from the tooth. After the IR-light is removed, the dental composition changes back to visually blending with the tooth. Thus, the color changing dental composition can be used for dental diagnostics Another embodiment of the present invention is a kit or two-part composition for use in making a color changing dental composition. The color changing dental composition is capable of blending with a color of a person's tooth, and also capable of a reversible color change. Accordingly, the two-part composition includes at least one dental composition configured for placement onto a person's tooth. Additionally, the two-part composition includes at least one anti-stokes up converter for combining with the at least one dental composition. As such, the combined dental composition is capable of a reversible color change when exposed to a long wavelength light.

An additional embodiment of the present invention is a method of performing a dental procedure. Such a dental procedure includes applying a color changing dental composition to a tooth. Accordingly, the dental composition is comprised of at least one polymerizable resin and at least one anti-stokes up converter. Under normal conditions the dental composition visually blends with the patients tooth. However, exposing the dental composition to IR-light can effect a reversible change in the color of the dental composition. Thus, the change in color can enable the dental professional to be able to distinguish the dental composition from the natural tooth.

These and other advantages and features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only typical embodiments of the invention and are therefore not to be considered limiting of its scope. The invention will be described and explained with additional specificity and detail through the use of the accompanying drawings in which.

DETAILED DESCRIPTION OF EMBODIMENTS OF THE INVENTION

Generally, embodiments of the present invention include dental compositions, two-part dental compositions, and associated methods of making or using the compositions. The terminology employed herein is used for the purpose of describing particular embodiments only and is not intended to be limiting.

As used herein, the term "color changing" refers to a substance that changes color, becomes luminescent, or changes to a contrasting shade when exposed to a certain stimulus or condition, and returns to the original color after the stimulus is removed. Examples of color changing substances include, without limitation, anti-stokes up converters, fluorescent materials, phosphorescent materials, photochromic materials, and thermochromic materials.

As used herein, the term "anti-stokes" and/or "up-converter" refers to a substance that can absorb long wavelength light such as IR-light and emit short wavelength light such as colored light to near UV-light. Accordingly, an anti-stokes material can absorb low energy photons and emit high energy photons. Without being bound to theory, it is thought that an anti-stokes material absorbs at least two low energy long wavelength photons, and emits a single high energy short wavelength photon. Thus, an anti-stokes up converter material converts lower energy light into high energy light. As such, an anti-stokes up converter material can appear colorless in white light, but emits visible color when exposed to IR-light.

As used herein, the term "fluorescent" refers to any substance that becomes luminescent when exposed to light. Typically, a fluorescent material can appear to slightly change color or emit color more brightly while being exposed to a UV-light stimulus, and cease to be luminescent when the UV-light is removed.

As used herein, the term "photochromic" refers to any substance that can change colors or become a contrasting shade when exposed to light. For example, a photochromic substance can originally appear to be clear or white, but darken to a grey color when stimulated by being irradiated with light. A photochromic substance will return to the original color after it is no longer being irradiated with light.

As used herein, the term "thermochromic" refers to any substance that can change color in response to heating or cooling. For example, a thermochromic substance may appear to have an original color or no color under a normal temperature, but change to emit a different color when stimulated by either being heated or cooled. A thermochromic substance will return to the original color after it returns to the normal temperature.

As used herein, the term "phosphorescent" or "phosphor" refers to any substance containing electrons which temporarily enter an excited state upon exposure to a source of energy, such as light, electricity, or heat, and emit photons of visible light as they return to an unexcited state thereby creating a luminescence that is still visible after the source of energy has been removed. As such, phosphorescent materials can glow in the dark.

As used herein, the term "dispersement" or "dispersing" refers to placing and distributing various color changing materials within a composition.

As used herein, the term "dispersing agent" refers to any substance that prevents color changing materials (particles) from agglomerating or otherwise settling out of a composition.

As used herein, the term "effective amount" refers to the minimal amount through the maximal amount of a substance or agent, which is sufficient to achieve a desired effect. For example, an effective amount of an anti-stokes up converter in a dental composition would be the minimum amount that provides the desired color change so that a dental professional can distinguish between the dental composition and the surrounding teeth.

As used herein, the term "white light" refers to broad spectrum light that can range from IR-light to UV-light. For example, the light emitted from the sun and regular light bulbs can be considered white light.

As used herein, the term "long wavelength light" refers to light having a wavelength that is at least as long as red light, and preferable light having a wavelength longer than red light. For example, infrared light (IR-light) is a long wavelength light.

As used herein, the term "normal conditions" refers to the ordinary conditions of temperature and light that exist in a mouth when it is open or closed in routine daily activities that commonly occur. For example, the opening and closing of a mouth during a conversation or a smile can be characteristic of "normal conditions."

It should be recognized that the chemical-nomenclature employed herein is used for convenience and brevity, and any of the elements recited additionally includes the monovalent or multivalent ions thereof. For example, erbium (Er) includes the element and the monovalent, divalent, trivalent, and other multivalent erbium ions, if the valence is possible.

Concentrations, amounts, particles sizes and other numerical data may be presented in a range format. It is to be understood that such a range format is used merely for convenience and brevity and should be interpreted flexibly to include not only the numerical values explicitly recited as the limits of the ranges, but also to include all the individual numerical values or sub-ranges encompassed within that range as if each numerical value and sub-range is explicitly recited. For example, the particle diameter range of about 0.5 micrometers to about 50 micrometers should be interpreted to include not only the explicitly recited limits of about 0.5 micrometers and about 50 micrometers, but also to include such individual diameters such as 1, 2, 10, and 20 micrometers as well as sub-ranges between these individual diameters. This interpretation should apply regardless of the breadth of the range or the characteristic being described, and should apply to ranges having both upper and lower numerical values as well as open-ended ranges reciting only one numerical value.

Dental compositions in accordance with embodiments of the present invention can include sealers, permanent fillings, temporary fillings, cements, varnishes, composites, adhesives, and the like. Accordingly, these dental compositions can be configured for being cured after being placed into the mouth such as for filling and sealing root canals. In one embodiment, dental compositions can be formulated for adhering veneers, inlays, onlays, crowns, pontics, bridges, or other prosthetics in the mouth. In another embodiment, the dental compositions can be used in orthodontics for affixing an orthodontic bracket to a tooth.

Generally, a dental composition in accordance with an embodiment of the present invention is formulated to blend with a person's tooth, and is capable of a changing color. The dental composition can include at least one polymerizable resin and at least one anti-stokes up converter admixed together and configured for placement on a person's tooth. The dental composition is formulated to blend with the person's tooth under natural conditions and/or white light. Additionally, the anti-stokes up converter enables the dental composition to be capable of changing color when exposed to long wavelength light.

In another embodiment of the present invention, a kit or two-part composition having a combination of compositions can be provided. Such a combination of compositions can include at least one dental composition configured for placement onto a person's tooth, and at least one composition comprised of at least one anti-stokes up converter. The at least one dental composition can be used for being combined with the anti-stokes up converter prior to being applied to the person's tooth. The combination of compositions can be formulated to blend with the person's tooth under normal conditions and/or white light. Additionally, the combination of compositions can be capable of changing color when exposed to long wavelength light.

Also, a dental composition can include any composition that is formulated to be combined with another composition prior to being fixedly applied to a tooth. As such, the resultant mixture of compositions can be properly formulated to adhere to a tooth, where the individual compositions may or may not have sufficient dental-compatibility or adherence.

Additionally, the dental composition can include solid prefabricated dental prostheses. Accordingly, a dental prosthesis such as a veneer, crown, inlay, onlay, pontic, or bridge can be prefabricated before being adhered to the patient's tooth. These dental prostheses can be comprised of a dental composite that has been cast into a solid form. Additionally, a dental prosthesis can be affixed to a tooth with an adherent dental composition such as a dental composition that includes an anti-stokes up converter. Alternatively, the dental prosthesis can include an anti-stokes up converter.

Accordingly, a wide variety of anti-stokes up converters can be included in the present invention. As such, any anti-stokes up converter that can be admixed into a dental composition that blends with teeth under white light or normal conditions, and then becomes visible after being exposed to light is contemplated to be included in the present invention. Accordingly, the anti-stokes up converters can be inorganic materials comprised of rare earth and lanthanide elements, which are commonly in crystal materials. Also, anti-stokes up converting materials can include anti-stokes up converter hosts, each doped with at least one activator or activator couple. Examples of up converter hosts can include: sodium yttrium fluorides (e.g., $NaYF_4$), lanthanum fluorides (e.g., $LaF_3$), lanthanum oxysulfides (e.g., $La_2O_2S$), yttrium oxysulfides (e.g., $Y_2O_2S$), yttrium fluorides (e.g., $YF_3$), yttrium gallates (e.g., $YGaO_3$ and $Y_3Ga_5O_{12}$), yttrium aluminum garnets (e.g., $Y_2Al_5O_{12}$), gadolinium fluorides (e.g., $GdF_3$), barium yttrium fluorides (e.g., $BaYF_5$ and $BaY_2F_8$), and gadolinium oxysulfides (e.g., $GdO_2S$). For example, suitable activators can include ytterbium (Yb), erbium (Er), holmium (Ho), terbium (Tb), thulium (Tm), and the like. Additionally, activator couples can include, for example, ytterbium:erbium, ytterbium:thulium, ytterbium:holmium, and the like. Without being bound to theory, it is thought that the absorber is ytterbium and the emitter is erbium, holmium, terbium, and thulium. For example, the absorber to emitter ratio can be 1:1, 3:1, 4:1, 5:1, 8:1, 9:1, 10:1, and 11:1 through 20:1. However, other ratios can perform as up converters.

For example, various up converter materials can be employed in the present invention such as the materials shown in Table 1.

TABLE 1

Anti-Stokes Up Converters

| Host material | Absorber Ion | Emitter Ion | Color |
|---|---|---|---|
| $Y_2O_2S$ | ytterbium | erbium | green |
| $Gd_2O_2S$ | ytterbium | erbium | red |
| $La_2O_2S$ | ytterbium | holmium | green |
| YOF | ytterbium | thulium | blue |
| $Y_3OCl_7$ | ytterbium | terbium | green |
| $YF_3$ | ytterbium | erbium | red |
| $GdF_3$ | ytterbium | erbium | green |
| $LaF_3$ | ytterbium | holmium | green |
| $NaYF_4$ | ytterbium | thulium | blue |
| $BaYF_5$ | ytterbium | thulium | blue |
| $BaY_2F_8$ | ytterbium | terbium | green |
| $YGaO_3$ | ytterbium | erbium | red |
| $Y_3Ga_5O_{12}$ | ytterbium | erbium | green |
| $YSi_2O_5$ | ytterbium | holmium | green |
| $YSi_3O_7$ | ytterbium | thulium | blue |

In addition to the materials in Table 1 and derivatives thereof, aluminates, phosphates, and vanadates can be suitable host materials. Additionally, many other variations of these materials that can include host materials, absorbers, and/or emitters can be used in the present invention. Additional examples of anti-stokes up converters include $CsCdBr_3:Er^{3+}$, $Y_2SiO_5:Pr^{3+}$, $Lu_2SiO_5:Pr^{3+}$, and $Gd_2SiO_5:Pr^{3+}$ crystals. It should be recognized that the above is not a complete listing of anti-stokes up converting materials that can be used in the present invention, and any anti-stokes up converter can be used in the present invention.

The anti-stokes up converters can be admixed into a dental composition in an amount sufficient for changing color, even if only slightly, when exposed to long wavelength light that induces the color change. Accordingly, a wide range of concentrations of anti-stokes up converters can be admixed or combined with dental compositions in order to achieve the desired visual effects. Additionally, the amount of anti-stokes up converting material can be determined by the amounts and nature of the other constituents in the composition. The dental composition is configured such that when it is exposed to low energy light, the anti-stokes up converter can emit a color that is distinguishable from the tooth for use in dental diagnostics.

In another embodiment, the anti-stokes up converters can be encapsulated in a glass. Accordingly, the anti-stokes up converters can be combined with $SiO_2$ under heat so that glass beads, glass microbeads, or bulk class with up conversion characteristics can be formed. For example, the glass can be comprised of silicon (Si), cerium (Ce), antimony (Sb), tin (Sn), zirconium (Zr), strontium (Sr), barium (Ba), aluminum (Al), zinc (Zn), and the like. When formed, the bulk class can then be ground or milled to produce anti-stokes up converter glass particles that can be formulated into a dental composition. It is thought, without being bound to theory, that encapsulating the anti-stokes up converter in a glass can increase the longevity of the up conversion characteristic, and prevent the anti-stokes up converters from leaching out of the dental composition. Additionally, the glass encapsulated anti-stokes up converters can increase biocompatibility of the color changing dental compositions.

Similarly, the anti-stokes up converters can be encapsulated within a polymeric microbead for much of the same reasons they can be encapsulated in a glass. In one embodiment the microbead can be comprised of hydrophobic monomers that are polymerized into crosslinked and/or non-crosslinked polymers. Examples of suitable hydrophobic polymers can include crosslinked and non-crosslinked polyacrylates such as polymethyl methacrylate, crosslinked and non-crosslinked polyaromatics such as polystyrene and polyvinyltoluene.

The anti-stokes up converters and/or anti-stokes up converter encapsulated materials can also be admixed with a dispersing agent to facilitate the dispersement and retention of the color changing materials in the composition. Examples of dispersing agents include polymers and copolymers of styrene sulfonate salts, acrylic and styrene copolymers, sulfonated polyesters, oleoyl methyl taurine, sodium dodecyl sulfate, amine dispersants, methyl stearate, ethyl stearate, methyl hexanoate, methyl heptanoate, methyl octanoate, methyl laureate, methyl oleate, methyl adipate, methyl caprylate, methyl caproate, methyl anthranilate, methyl palmitate, methyl palmitoleate, methyl oxalate, methyl 2-nonanoate, methyl benzoate, 2-methylbenzophenone, methyl behenate, methyl benzilate, methylbenzyl acetate, trimethyl borate, methyl caproate, methyl butyrate, methyl decanoate, methyl cyclohexanecarboxylate, methyl dimethoxyacetate, methyl diphenylacetate, methyl enanthate, methyl heptanoate, methyl linoleate, and the like.

Additionally, the dental composition can include other color changing components. The use of an additional color changing component can provide the dental composition with an additional color changing feature that can aid in dental diagnostics. Examples of color changing substances that can be included in a dental composition can include fluorescent materials, thermochromic materials, photochromic materials, and phosphorescent materials. Additionally, these other color changing components can be encapsulated in a glass or microbead.

The dental compositions can include a variety of materials such as polymerizable resins, polymerization initiators, fillers, coupling agents, plasticizers and the like. The polymerizable resin can include monomers, oligomers, and polymers having one or more ethylenically unsaturated groups. The ethylenically unsaturated groups can be polymerized by free radial polymerization. Such free radical polymerizable materials include monomers and/or mono-, di- or poly-acrylates and methacrylates. For example, the polymerizable resin can include methyl acrylate, methyl methacrylate, ethyl acrylate, isopropyl methacrylate, n-hexyl acrylate, stearyl acrylate, allyl acrylate, glycerol diacrylate, glycerol triacrylate, ethyleneglycol diacrylate, diethyleneglycol diacrylate, triethyleneglycol dimethacrylate, diurethane dimethacrylate, 1,3-propanediol diacrylate, 1,3-propanediol dimethacrylate, trimethylolpropane triacrylate, 1,2,4-butanetriol trimethacrylate, 1,4-cyclohexanediol-diacrylate, pentaerythritol triacrylate, pentaerythritol tetraacrylate, pentaerythritol tetramethacrylate, sorbitol hexacrylate, the diglycidyl methacrylate of bis-phenol ("Bis-GMA"), bis[1-(2-acryloxy)]-p-ethoxyphenyldimethylmethane, bis[1-(3-acryloxy-2-hydroxy)]-p-propoxyphenyldimethylmethane, trishydroxyethyl-isocyanurate trimethacrylate, the bis-acrylates and bis-methacrylates of polyethylene glycols of molecular weight 200-500, copolymerizable mixtures of acrylated monomers, and copolymerizable acrylated oligomers, and the like. Also, vinyl compounds such as styrene, diallyl phthalate, divinyl succinate, divinyl adipate, and divinylphthalate can be polymerized. Additionally, mixtures of two or more of these free radically polymerizable materials can be used if desired. Alternatively, phosphoric acid derivatives and carboxylic acid derivatives of these ethylenically unsaturated monomers can be used. However, it should be recognized that this is not an exhaustive listing of polymerizable resins, and other polymerizable resins can be used in accordance with the present invention.

A polymerizable resin can be included in the dental composition over a wide range of concentrations. The concentration can depend on the amount of filler, plasticizer, and polymerization initiator as well as other factors. For example, the dental composition can have a polymerizable resin such as an ethylenically unsaturated monomer at a preferred range of from about 10% to about 99% by weight, more preferred range of from about 15%-80% by weight, and most preferred range of from about 25% to about 50% by weight.

Typically, free radical polymerization requires the generation of a free radical from an initiator. Various types of initiators can produce a free radical upon being exposed to light, heat, or chemicals. The initiator compounds are provided into the dental compositions of the invention in an effective amount to initiate polymerization or enhance the rate of polymerization or curing.

Photo-initiators are a group of compounds that will generate a free radical when exposed to light having a specific wavelength. As such, different photo-initiators can be selected depending on the wavelength of light that will initiate the polymerization. Examples of photo-initiators can include benzo-phenone, benzoin, 9,10-phenanthrenequinone, diacetyl, furil, anisil, 4,4'-dichlorobenzil, 4,4'-dialkoxybenzil, phenylpropanedione, acylphosphine oxides, camphorquinone, derivatives thereof, and the like. Photo-polymerization can be initiated, for example, by irradiation with light having a wavelength of from about 400 nm to about 500 nm.

Heat-initiators can be used in hot-curing systems, which is particularly suitable for producing dental prostheses such as crowns, inlays and onlays. Some heat-initiators can be activated with temperatures less than 150° C. Examples of heat-initiators can include t-butyl peroxide, dibenzoyl peroxide, dilauroyl peroxide, t-butyl peroctoate, t-butyl perbenzoate, and the like.

On the other hand, in certain applications a chemical-initiator, which typically is comprised of at least two co-initiators that generate a free radical, can be preferred to induce polymerization. These chemical-initiator systems can use a reactive pair. For example, benzoyl peroxide, lauryol peroxide, or dibenzoyl peroxide can be used in combination with a N,N-dimethyl-p-toluidine, N,N-dihydroxyethyl-p-toluidine, or other similar amines. Alternatively, a combined system including a photo-initiator, heat-initiator, and/or chemical-initiator can be used.

The concentration of the polymerization initiator depends on the concentration of the polymerizable resin, or more particularly on the concentration of the ethylenically unsaturated monomers. Additionally, the concentration of the polymerization initiator depends on the type of initiator. For example, the dental composition can include a polymerization initiator at a preferred range of from about 0.001% to about 5% by weight, more preferred range of from about 0.01% to about 2.5% by weight, and most preferred range of from about 0.1% to about 1% by weight. However, the concentration of initiator can be varied depending on the type of initiator and/or type of resin as well as the desired properties of the composition.

In another embodiment, a dental composition can include a filler to impart radiopaque, radiolucent, or nonradiopaque visual characteristics to the composition. The particles can include organic materials and inorganic materials. Examples of organic fillers include pulverized polycarbonates, polyepoxides, and the like. Additionally, polymeric particles or microbeads comprised of homopolymers or heteropolymers of the monomers described herein can be used as organic fillers. Also, mixtures of fillers can be used.

Examples of inorganic fillers are naturally-occurring or synthetic materials such as quartz, nitrides (e.g., silicon nitride), colloid silica, feldspar, borosilicate, kaolin, talc, ytterbium trifluoride, and various glasses. The glasses can be comprised of, for example, silicon (Si), cerium (Ce), antimony (Sb), tin (Sn), zirconium (Zr), strontium (Sr), barium (Ba), aluminum (Al), zinc (Zn), and the like. More particularly, some glasses can be oxides of these materials.

In one embodiment, the composition can include a filler at a preferred range of from about 0% to about 90% by weight, more preferred range of from about 0% to about 50% by weight, and most preferred range of from about 0% to about 25%. The filler can be comprised of particles having a preferred diameter range of from about 0.005 micrometers to about 50 micrometers, more preferred range of from about 0.5 micrometers to about 25 micrometers, or most preferred range of from about 1 micrometer to about 10 micrometers. For alternative embodiments it may be more preferable for the fillers having an average particle size of from about 0.005 micrometers to about 2 micrometers can be used. However, larger or smaller particles sizes can be used. Additionally, x-ray opaque fillers having particles sizes less than 5 micrometers such as ytterbium trifluoride and the like can impart beneficial characteristics to the tooth.

In order to enhance the bond between the filler and the dental composition, a coupling agent can optionally be used. Examples of coupling agents can include, without limitation, gamma-methacryloxypropyltrimethoxysilane, gamma-mercaptopropyltriethoxysilane, beta-(3,4-epoxycyclohexyl)-ethyltrimethoxysilane, gamma-glycidoxypropyltrimethoxysilane, and the like.

Various other additives can be included within the dental composition in accordance with the present invention. These additives can include stabilizers, UV absorbers, polymerization accelerants, polymerization inhibitors, dyes, pigments, and lubricants. Additionally, the dental compositions can include flavorants, anti-microbials, fragrance, viscosity modifiers, rheology modifiers, fluoride releasing materials, and plasticizers.

Another embodiment of the present invention provides a method of performing a dental procedure; The method includes applying a dental composition to a tooth, where the dental composition is comprised of at least one polymerizable resin and at least one anti-stokes up converter. Additionally, the method includes exposing the dental composition to a long wavelength light so that the dental composition changes from blending with the tooth to a color that contrasts with the tooth. More particularly, the method includes irradiating the dental composition with JR-light so that a visible color is emitted from the dental composition. After the dental composition up converts low energy light to emit a higher energy light, the dental composition can be distinguished from the natural tooth.

Figure 1A:
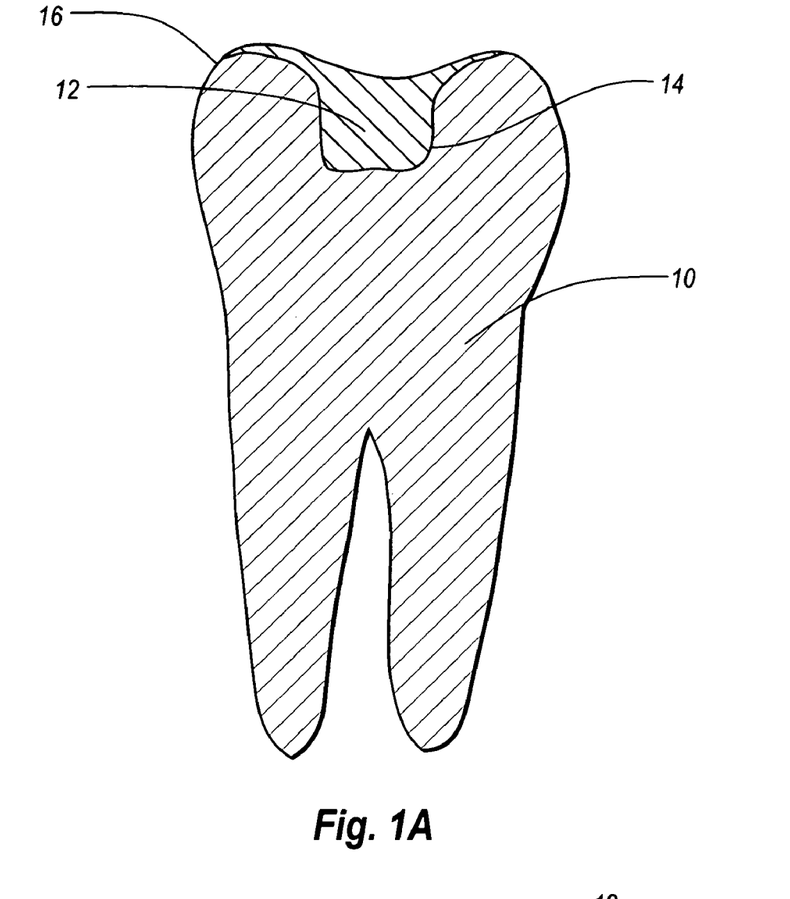
FIG. 1A is a side view of a tooth with a cavity that is filled with a color changeable filling dental composition.
Figure 1B:
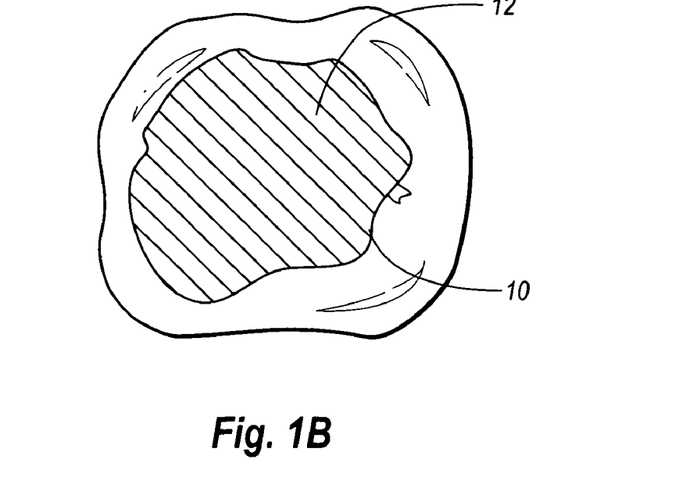
FIG. 1B is a top view of the tooth in FIG. 1A.

FIGS. 1A and 1B depict an embodiment of the present invention that includes a tooth 10 having a dental composition 12 applied thereto. More particularly, during a dental procedure the tooth 10 has a cavity 14 that has been prepared by a dental professional. As such, the dental composition 12, which includes a polymerizable resin and an anti-stokes up converter, can be configured into a filling 12 for use in treating the cavity 14. After the cavity 14 has been filled, the filling 12 can be exposed to a long wavelength light for a sufficient duration in order to change the tooth-blending dental composition to a visible color. After the dental composition changes color by emitting up converted light, the dental professional can then distinguish between the dental composition and the natural tooth. In some instances the dental professional may determine that the tooth 10 has superfluous portions 16 of dental material.

Figure 2A:
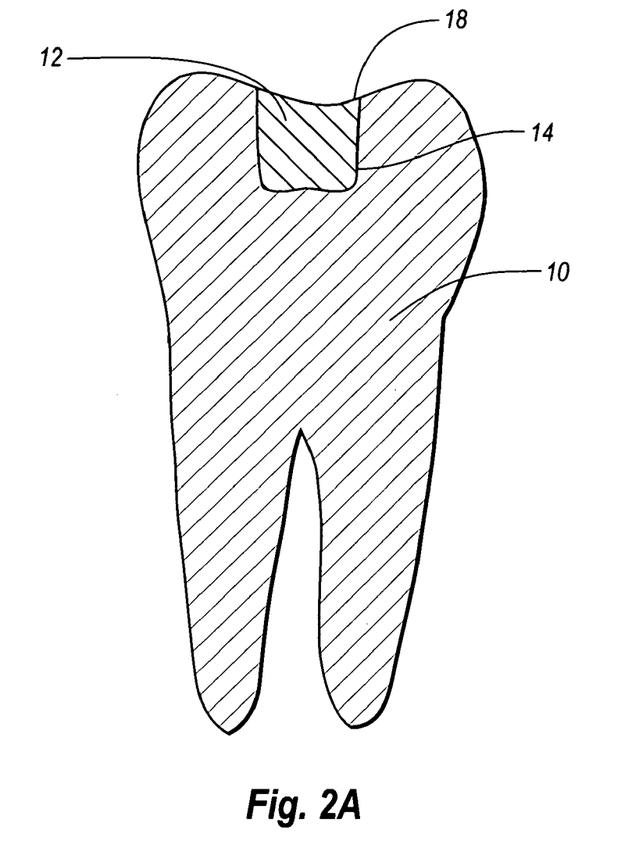
FIG. 2A is a side view of a tooth with a cavity that is filled with a color changeable filling dental composition.
Figure 2B:
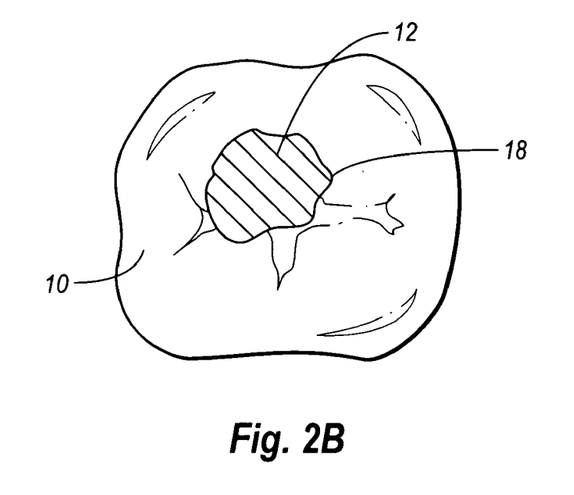
FIG. 2B is a top view of the tooth in FIG. 2A.

In another embodiment of the present invention depicted in FIGS. 2A and 2B, the dental professional can remove the superfluous portion (as depicted in FIGS. 1A and 1B) from the tooth 10 during a dental procedure. Since the up converted light can be emitted from the dental composition and visualized prior to curing the dental composition on the tooth, the superfluous portion can be easily removed prior to polymerization of the resin. Alternatively, the superfluous portion can be removed after the resin has been cured on the tooth 10. This can be done by grinding or other procedures known and practiced by dental professionals. As such, the tooth 10 can be treated so that the filling 12 fills the cavity 14 to conform to typical dental standards. After this is complete, the dental professional can visualize the boundary 18 between the filling 14 and the tooth by changing the color of the dental composition in order to make sure the treatment is sufficient.

Figure 3A:
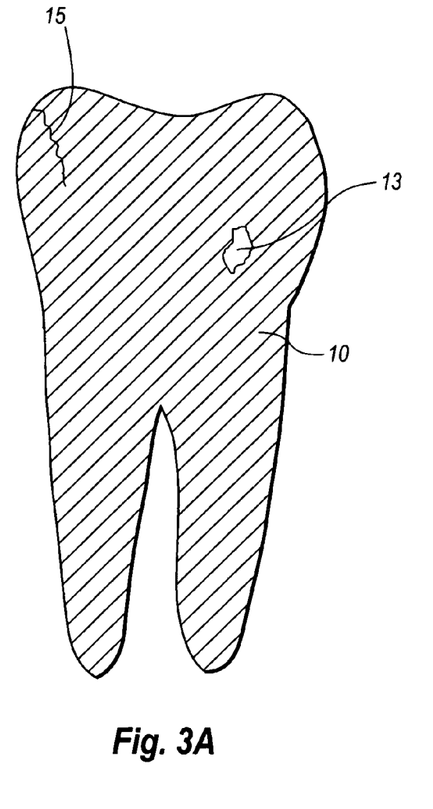
FIG. 3A is a top view of a tooth with a pit and fissure.
Figure 3B:
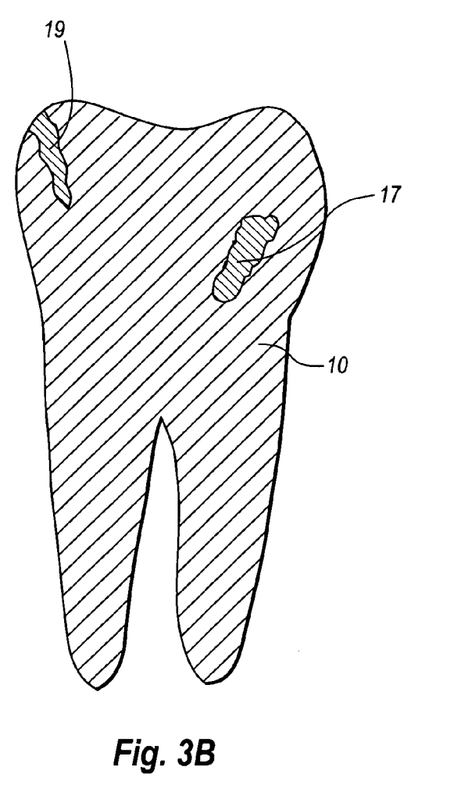
FIG. 3B is a top view of the tooth in FIG. 3A with the pit and fissure restored with a color changing sealant.

Additionally, FIGS. 3A and 3B depict another embodiment of the present invention that includes repairing a tooth 10 having a pit 13 and fissure 15. During a dental procedure a dental professional can identify the location of a pit 13 or fissure 15 in a tooth 10. Accordingly, a dental composition having an anti-stokes up converter can be configured into a sealant. The dental professional can apply the pit sealant 17 over the pit 13. Also, the dental professional can apply the fissure sealant 19 to the tooth 10 so as to seal the fissure 15. In any event, the dental professional can expose the pit sealant 17 and/or the fissure sealant 19 to long wavelength light to cause the sealant to emit shorter wavelength light.

Figure 4A:
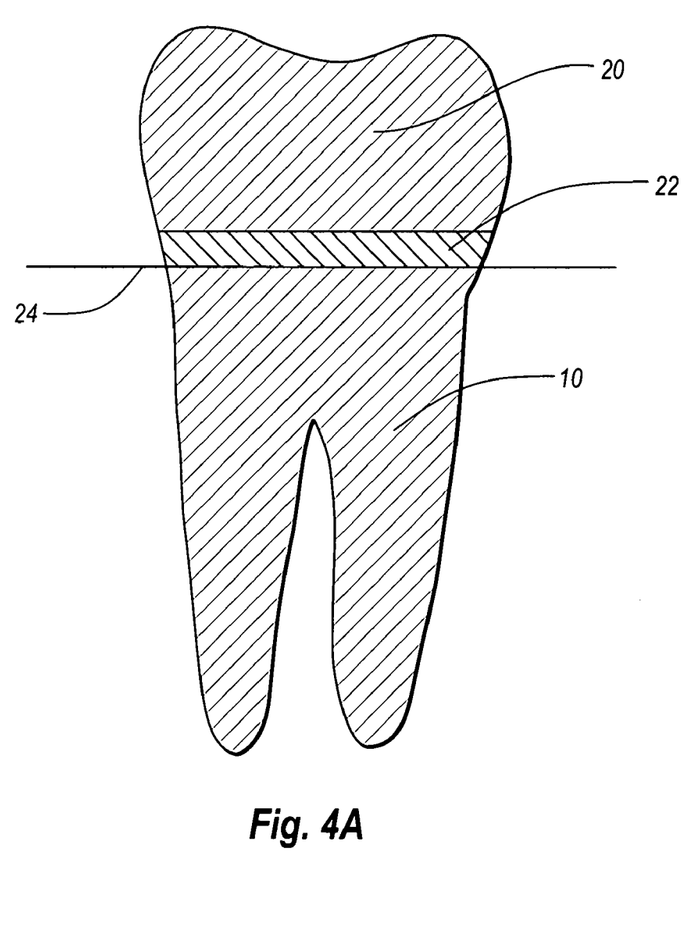
FIG. 4A is a side view of an embodiment of a dental procedure where a crown is being placed onto a tooth with a color changeable prosthetic adhesive.
Figure 4B:
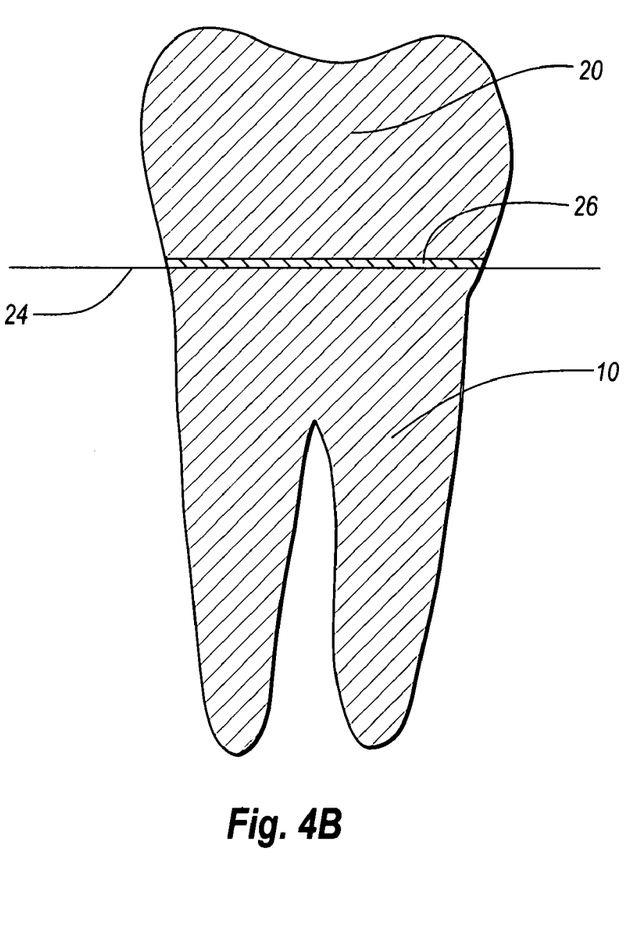
FIG. 4B is a side view of an embodiment of a dental procedure where a crown is affixed to a tooth.

FIGS. 4A and 4B depict another embodiment of the present invention that includes affixing a crown 20 to the tooth 10 during a dental procedure. Accordingly, a dental composition 22 including a polymerizable resin and at least one anti-stokes up converter are admixed together and configured into a prosthetic adhesive 22. The adhesive 22 is applied such that it is between the tooth 10 and the crown 20 when the crown 20 is being positioned onto the tooth 10, as depicted in FIG. 4A. Usually, the crown 20 will be affixed so that it is above or at the gum line 24. Alternatively, the dental prosthesis can also be comprised of an anti-stokes up converter.

After the crown 20 is affixed to the tooth, as depicted in FIG. 4B, a visible boundary 26 may exist. The visible boundary 26 may be observed to distinguish the crown 20 from the tooth 10. In order for better distinguish the crown 20 from the tooth 10, some of the adhesive may be present at the visible boundary 26. As such, the visible boundary 26 may be capable of changing color by up converting long wavelength light to shorter wavelength light. Alternatively, the visible boundary 26 may not be capable of changing color. Additionally, if any superfluous prosthetic adhesive is forced out from between the crown 20 and the tooth, it may be removed before or after curing.

Figure 5A:
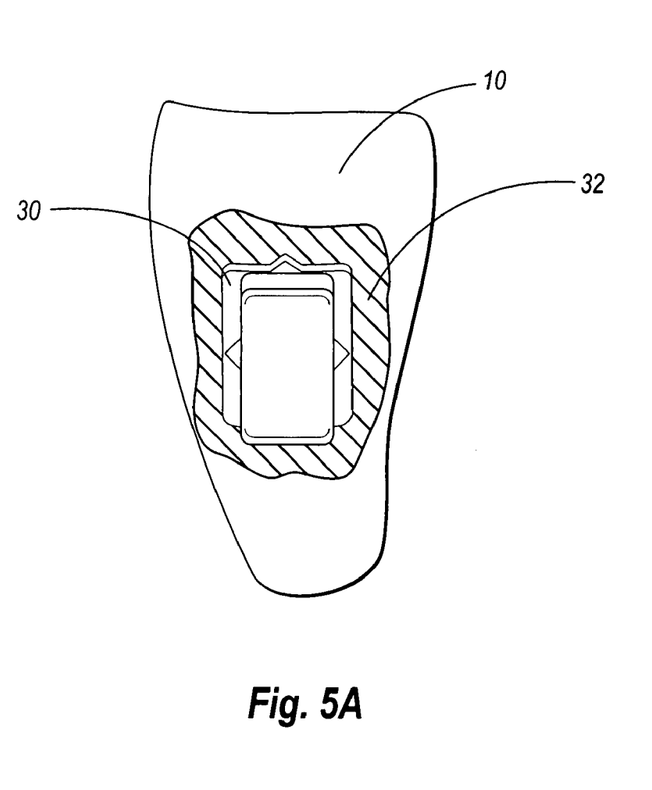
FIGS. 5A and 5B are side views of an orthodontic bracket adhered to a tooth with a color changeable bracket adhesive.
Figure 5B:
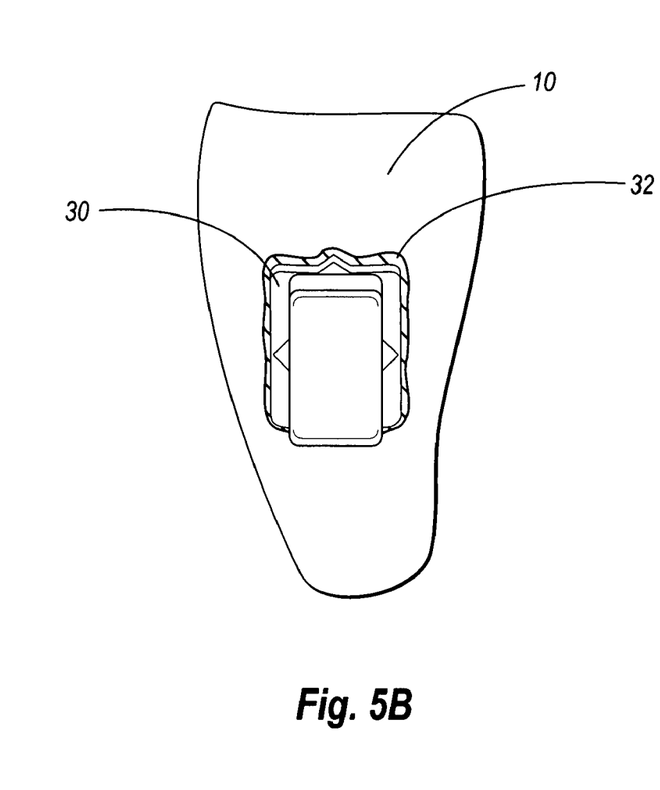

Another embodiment of the present invention that includes affixing an orthodontic bracket 30 to a tooth 10 is depicted in FIGS. 5A and 5B. The orthodontic bracket can be adhered to a tooth with a bracket adhesive having a polymerizable resin and at least one anti-stokes up converter. As such, the dental procedure can include applying an anti-stokes up converter containing bracket adhesive 32 to the tooth 10. Alternatively, the bracket adhesive 32 can be applied directly to the bracket 30. The bracket 30 is then applied to the tooth 10, and positioned into a correct orientation with respect to the tooth and other brackets on the surrounding teeth. After the bracket 30 has been placed on the tooth 10, the dental professional can determine if there is any extraneous or superfluous adhesive 32 around the bracket 30, as depicted in FIG. 5A. Accordingly, the adhesive 32 can be exposed to a long wavelength light stimulus so that the adhesive can change from blending with the tooth to emitting a visible color. Thus, as depicted in FIG. 5B, any superfluous adhesive 32 can be removed before or after curing.

Figure 6A:
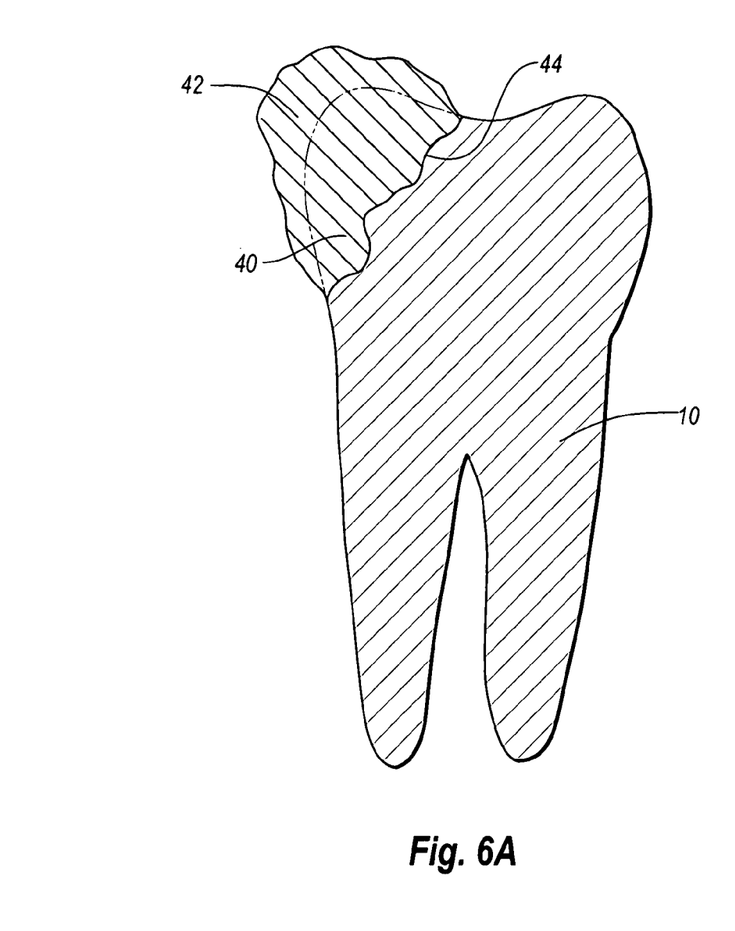
FIGS. 6A and 6B are side views of a tooth having a color changeable dental restorative composition.
Figure 6B:
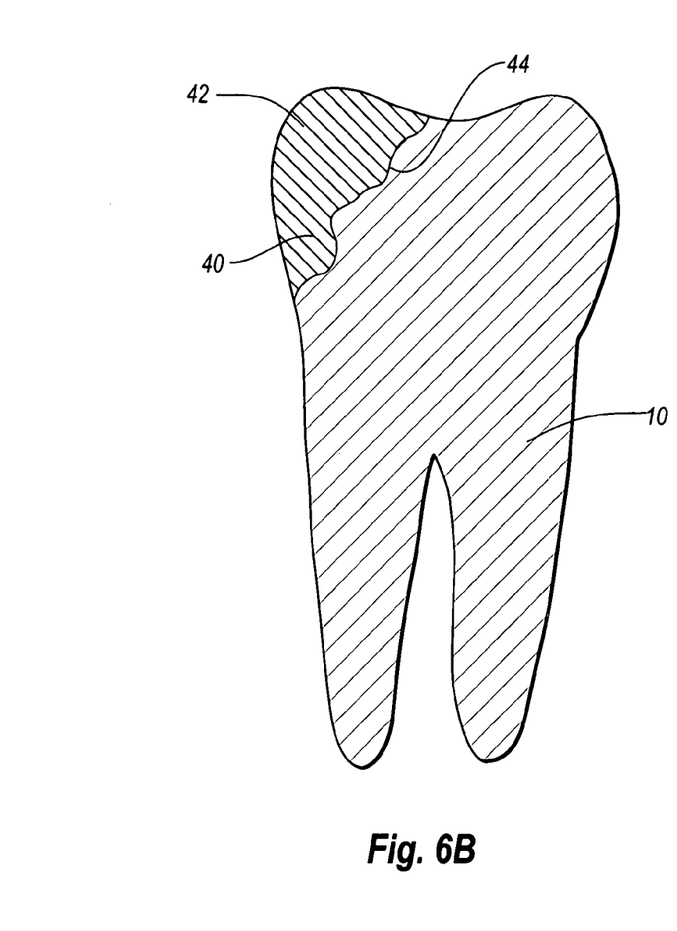

FIGS. 6A and 6B depict another embodiment of the present invention that includes applying a dental restorative composition 40 to the tooth 10. The dental restorative composition 40 can include at least one polymerizable resin and at least one anti-stokes up converter. During the dental procedure, the dental restorative composition 40 can be applied to the tooth 10, and cured into place. However, it is possible that too much of the restorative composition 40 can be present on the tooth 10 so that a superfluous portion 42 needs to be removed, as depicted in FIG. 6A. In order to facilitate determining how much needs to be removed, the dental professional can irradiate the restorative composition 40 with long wavelength light so that it will be capable of emitting a visible color. As such, changing the dental composition from blending with the tooth to emitting visible light can aid in identifying the amount of restorative composition 40 needs to be removed.

Accordingly, it may be determined that a superfluous portion 42 of the restorative composition 40 needs to be removed. As such, the dental procedure can include shaping the restorative composition 40 into a correctly shaped dental restoration 46 as depicted in FIG. 6B. The shaping can be preformed before the restorative composition 40 has been cured. Alternatively, the shaping can be performed after the restorative composition 40 has been cured into a hardened dental restoration 46.

After the dental diagnostic procedure has be completed for any methods or dental procedures that utilize a dental composition including an anti-stokes up converter, the dental professional can terminate the process of irradiating the dental composition with long wavelength or IR-light. As such, the IR-light source can be extinguished so that the dental composition is no longer being exposed to IR-light, and the anti-stokes up converters no longer emit visible light. Consequently, the dental composition can then convert back to blending with the patient's teeth. Thus, the dental composition can reversibly change colors for use in dental diagnostics, and then return to the original teeth-blending color.

Subsequent to any of the procedures described, a dental professional may need to distinguish between a dental composition and the tooth after the composition has been in place for some time. Accordingly, the dental professional exposes the dental composition to long wavelength or IR-light so that the dental composition emits visible light that can be viewed by the dental professional. When the dental professional sees the dental composition emit the visible light, the dental composition will be distinguishable from the natural tooth. Accordingly, a boundary between the dental composition and the natural tooth can be visualized by the dental professional so that they will be able to identify the interface between the dental composition and the natural tooth. Identifying the interface, which emits a color contrasting with the tooth, can aid the dental professional in not removing any, or a significant amount, of the tooth during the process of removing the dental composition. For example, if the dental restorative depicted in FIG. 6B needs to be removed and/or replaced, anti-stokes up converters can be used to enable the dental professional to remove the dental restorative without removing too much of the tooth. Thus, the removal can be performed until the tooth does not exhibit a change in color when being exposed to long wavelength or IR-light.

Optionally, a method of performing a dental procedure can also include using a dental composition that includes at least another color changing substance or second color changing substance other than an anti-stokes up converter. Additionally, the dental composition can be exposed to a second color changing stimulus for a sufficient duration to effect a second color change. The second color changing stimulus can be any stimulus that induces a color change in a substance other than an anti-stokes up converter. The inclusion of a second color changing substance provides the dental professional with another way of distinguishing between the natural tooth and the dental composition. This can be helpful if the dental professional is not equipped with IR-light, or the anti-stokes material has somehow lost its ability to up convert absorbed IR-light into emitted visible light.

In accordance with the method of performing a dental procedure as described herein, when the second color changing material is a fluorescent material the second color changing stimulus is a light source such as an UV-light source. As such, the color change can be induced by irradiating the dental composition with a light source so that the color change is observable. Additionally, the color change can be reversed by removing the light source so that the dental composition changes back to the original color.

Additionally, when the second color changing material is a photochromic material; the second color changing stimulus is irradiating the dental composition with a light source, were the wavelength of the light, the intensity of the light, and the duration required to effect the color change can be varied in accordance with the photochromic material. Accordingly, the dental composition can be formulated so that a certain light source stimulus can be used. The dental composition can change back to the original teeth-blending color when the photochromic material stimulating light source is removed.

In an alternative embodiment, when the second color changing material is a thermochromic material, the second color changing stimulus can be either heating or cooling the dental composition so that the temperature changes from normal oral temperatures. As used herein, heating includes increasing the temperature of the dental composition to a temperature above 37° C., and cooling includes decreasing the dental composition to a temperature below 37° C. However, it may be possible to have a dental composition that will change to one color when heated, and then change to another color when cooled. After the temperature has been changed away from normal oral temperatures, the dental composition can be observed to change colors so that the dental professional can distinguish between the dental composition and the tooth. After the dental diagnostics have been performed, the temperature can be changed back to about 37° C. so that the dental composition can again blend with the surrounding teeth.

In another embodiment, when the second color changing material is a phosphorescent material, the second color changing stimulus can be a light source that emits any wavelength of visible or UV-light. Accordingly, the light source can emit any wavelength of light so long as it energizes the phosphorescent material to a level that enables phosphorescent luminescence to be emitted from the dental composition after the intensity of the light is sufficiently decreased or the light source is removed. Additionally, the method can be further comprised of removing the color changing, stimulus and/or decreasing the intensity of the light source so that the phosphorescence being emitted from the dental composition can be visualized. After the intensity of the light source has been decreased, a dental professional can visualize the phosphorescence being emitted from the dental composition. Alternatively, phosphorescence can be seen while a phosphorescent material is being irradiated with UV-light. After the dental composition has not been irradiated with light for some period of time, the dental composition will cease being phosphorescent and blend with the natural tooth.

The present invention is further exemplified in the following examples, which are offered by way of illustration and are not intended to limit the invention in any manner.

EXAMPLE 1

A light-curable dental composition having color changing capabilities is formulated for use as a filling. A mixture is formed by mixing UC-3 Red (anti-stokes up converter, Artemis US Importers, LLC) at 1% by weight of the final composition with 23% by weight Bis-GMA. The mixture is processed with 50% by weight barium silicate glass powder, 5% by weight barium fluorosilicate glass powder, 5% by weight pyrogenic silica, and 15% by weight ytterbium trifluoride to produce a homogeneous composite. Additionally, 0.7% by weight camphorquinone, 0.1% by weight hydroquinone monoethyl ether, and 0.2% by weight ethyl-4-dimethylaminobenzoate are admixed into the homogeneous composite.

The homogeneous composite is applied to an artificial tooth as a filling, and cured by 4 minutes of irradiation with light at a wavelength of 400-500 nm. After curing, the filling material is exposed to IR-light. It is expected that the IR-light will cause the filing to emit a red color, and the artificial tooth will not change color under the IR-light.

EXAMPLE 2

A light-curable orthodontic bracket adhesive is prepared in accordance with the present invention. A mixture is prepared by mixing UC-8 Green (anti-stokes up converter, Artemis US Importers, LLC) at 1% by weight of the final composition with 88% by weight Bis-GMA. The mixture is then processed with 10% by weight silanized barium glass powder. Additionally, 0.5% by weight camphorquinone, 0.2% by weight hydroquinone monoethyl ether, and 0.3% by weight ethyl-4-dimethylaminobenzoate are admixed into the composition to form a bracket adhesive.

The bracket adhesive is applied to an artificial tooth, and cured by irradiation with light at a wavelength of 470 nm for 3 minutes. After curing, the bracket adhesive is exposed to IR-light. It is expected that the IR-light will cause the bracket adhesive to emit a green color, and the artificial tooth will not change color.

EXAMPLE 3

A light-curable dental sealant is prepared in accordance with the present invention. A mixture is prepared by mixing UC-60 Blue (anti-stokes up converter, Artemis US Importers, LLC) at 1% by weight of the final composition with 7-amino-4-methylcoumarin at 0.2% by weight. Additionally, 62% by weight Bis-GMA and 36% by weight triethylene glycol dimethacrylate are mixed into the mixture. Additionally, 0.4% by weight camphorquinone, 0.2% by weight hydroquinone monoethyl ether, and 0.2% by weight ethyl-4-dimethylaminobenzoate are admixed with the composition to form a color changing dental sealant.

The dental sealant is applied to an artificial tooth, and cured by irradiation with light at a wavelength of 400-500 nm for 3 minutes. After curing, the dental sealant is exposed to IR-light. It is expected that the IR-light will cause the dental sealant to emit a blue color, and the artificial tooth will not change colors. Additionally, the dental sealant is then exposed to UV-light. It is expected that the UV-light will cause the dental sealant to emit a violet-blue fluorescence, and the artificial tooth will not change colors.

The present invention may be embodied in other specific forms without departing from its spirit or essential characteristics. The described embodiments and examples are to be considered in all respects only as illustrative and not restrictive. The scope of the invention is, therefore, indicated by the appended claims rather than by the foregoing description. All derivatives which come within the meaning and range of equivalency of the claims are to be embraced within their scope.

What is claimed is:

1. A method of performing a dental procedure, the method comprising:
 applying a dental composition to a tooth, the dental composition being comprised of at least one polymerizable resin and at least one anti-stokes up converter, the anti-stokes up converter being adapted so as to convert long wavelength JR-light into shorter wavelength visible light,
 the anti-stokes up converter being comprised of at least one up converter host and at least one of an activator or activator couple,
 the dental composition blending with the tooth in the absence of being irradiated with IR-light; and
 wherein the at least one up converter host is selected from the group consisting of sodium yttrium fluorides, lanthanum fluorides, lanthanum oxysulfides, yttrium oxysulfides, yttrium fluorides, yttrium gallates, yttrium aluminum garnets, gadolinium fluorides, barium yttrium fluorides, and gadolinium oxysulfides, and the at least one activator is selected from the group consisting of ytterbium, erbium, holmium, terbium, and thulium, and the at least one activator couple is selected from the group consisting of ytterbium:erbium, ytterbium:thulium, ytterbium:terbium, and ytterbium:holmium, exposing the dental composition to JR-light to effect a reversible change in the color of the dental composition in order for the dental composition to temporarily visually contrast with the tooth.

2. A method in accordance with claim 1, further comprising visualizing the dental composition change from blending with the tooth to a contrasting color.

3. A method in accordance with claim 1, further comprising removing a superfluous portion from the dental composition.

4. A method in accordance with claim 1, further comprising affixing one of a dental prosthesis and an orthodontic bracket to the tooth.

5. A method in accordance with claim 1, further comprising shaping the dental composition into a dental restoration.

6. A method in accordance with claim 1, further comprising removing the dental composition from the tooth.

7. A method in accordance with claim 1, wherein the dental composition further comprises a color changing material that does not convert long wavelength IR-light into shorter wavelength visible light, the second color changing material selected from the group consisting of a fluorescent material, phosphorescent material, photochromic material, and thermochromic material, and the method further comprises exposing the dental composition to a second color changing stimulus which is not IR-light so that the second color changing material changes the color of the dental composition.

* * * * *

UNITED STATES PATENT AND TRADEMARK OFFICE
CERTIFICATE OF CORRECTION

PATENT NO.        : 7,314,610 B2                                        Page 1 of 1
APPLICATION NO.   : 11/066013
DATED             : January 1, 2008
INVENTOR(S)       : Dan Loveridge It is certified that error appears in the above-identified patent and that said Letters Patent is hereby corrected as shown below:

Column 3
Line 7, change "top view" to -- side view --
Line 8, change "top view" to -- side view --

Column 7
Line 59, change "radial" to -- radical --

Column 10
Line 39, change "tooth by" to -- tooth 10 by --

Column 11
Line 48, change "40 needs" to -- 40 that needs --
Line 53, change "46" to -- 44 --
Line 57, change "46" to -- 44 --

Column 12
Line 56, change "were" to -- where --

Column 14
Line 52, change "JR" to -- IR --
Line 57, paragraph starting "wherein the at least…" on line 59 should begin on line 57 before paragraph starting "the dental composition…"

Column 15
Line 4, change "JR" to -- IR --

Signed and Sealed this

Ninth Day of September, 2008

JON W. DUDAS
*Director of the United States Patent and Trademark Office*